(12) United States Patent
Ho et al.

(10) Patent No.: US 9,645,121 B2
(45) Date of Patent: May 9, 2017

(54) NONLINEAR DYNAMIC FOCUSING CONTROL METHOD

(71) Applicant: Industrial Technology Research Institute, Hsinchu (TW)

(72) Inventors: Chung-Lien Ho, Hsinchu (TW); Ren-Jr Chen, Hsinchu (TW)

(73) Assignee: Industrial Technology Research Institute, Chutung Township, Hsinchu County (TW)

( * ) Notice: Subject to any disclaimer, the term of this patent is extended or adjusted under 35 U.S.C. 154(b) by 628 days.

(21) Appl. No.: 14/150,171

(22) Filed: Jan. 8, 2014

(65) Prior Publication Data

US 2014/0334267 A1 Nov. 13, 2014

(30) Foreign Application Priority Data

May 7, 2013 (TW) .............................. 102116164 A (51) Int. Cl.
*G01N 29/34* (2006.01)
*G01N 29/26* (2006.01)
*G01N 29/06* (2006.01)

(52) U.S. Cl.
CPC ....... *G01N 29/262* (2013.01); *G01N 29/0654* (2013.01); *G01N 2291/02491* (2013.01)

(58) Field of Classification Search
CPC .................................................... G01N 29/34
USPC ....................................................... 367/138
See application file for complete search history.

(56) References Cited

U.S. PATENT DOCUMENTS

| 4,173,007 | A | | 10/1979 | McKeighen et al. |
| 4,469,009 | A | | 9/1984 | Takayama et al. |
| 4,983,970 | A | | 1/1991 | O'Donnell et al. |
| 5,111,695 | A | | 5/1992 | Engeler et al. |
| 5,331,885 | A | * | 7/1994 | Lassota ................. A47J 31/057 |
| | | | | 99/283 |

(Continued)

FOREIGN PATENT DOCUMENTS

| CN | 101571510 | 11/2009 |
| CN | 102297761 | 12/2011 |

(Continued)

OTHER PUBLICATIONS

Kuo et al., "Point Source and δ function", May 31, 2009, pp. 39-43.

(Continued)

*Primary Examiner* — Luke Ratcliffe
*Assistant Examiner* — Amie M N'Dure
(74) *Attorney, Agent, or Firm* — Muncy, Geissler, Olds & Lowe, P.C.

(57) ABSTRACT

A nonlinear dynamic focusing control method includes: (1) using a minimum length in a scan line having the minimum length and a maximum length as an initial location and assigning a focal point on the scan line; (2) calculating half depth of focus of the focal point, and the initial location plus the half depth of focus of the focal point being the location of this focal point on the scan line; (3) determining an initial calculation location of the next focal point by adding the half depth of focus of the focal point from the location of this focal point on the scan line in the direction of the maximum length; and (4) determining if the initial calculation location of the next focal point is greater than the maximum length.

15 Claims, 9 Drawing Sheets

(56) References Cited

U.S. PATENT DOCUMENTS

| | | | |
|---|---|---|---|
| 5,345,426 | A | 9/1994 | Lipschutz |
| 5,357,962 | A | 10/1994 | Green |
| 5,488,588 | A | 1/1996 | Engeler et al. |
| 5,501,219 | A | 3/1996 | Phelps et al. |
| 5,522,391 | A | 6/1996 | Beaudin et al. |
| 5,836,881 | A | 11/1998 | Bae |
| 6,097,856 | A * | 8/2000 | Hammond, Jr. ... G02B 27/0075 382/312 |
| 6,789,472 | B2 | 9/2004 | Nakamura et al. |
| 2003/0114962 | A1 * | 6/2003 | Niemeyer .......... A61B 1/00149 700/245 |
| 2005/0101863 | A1 | 5/2005 | Kawagishi et al. |
| 2007/0016039 | A1 | 1/2007 | Vortman et al. |
| 2007/0083110 | A1 * | 4/2007 | Lin .................. A61B 8/08 600/437 |
| 2009/0088644 | A1 * | 4/2009 | Yao .................. A61B 8/54 600/459 |
| 2009/0299184 | A1 | 12/2009 | Walker et al. |
| 2010/0242613 | A1 | 9/2010 | Simard et al. |
| 2010/0249594 | A1 * | 9/2010 | Magee .............. G10K 11/346 600/443 |
| 2012/0083695 | A1 | 4/2012 | Napolitano et al. |

FOREIGN PATENT DOCUMENTS

| | | |
|---|---|---|
| CN | 102809610 | 12/2012 |
| TW | 513613 B | 12/2002 |
| TW | 577986 B | 3/2004 |
| TW | I275382 B | 3/2007 |
| TW | I380014 | 12/2012 |

OTHER PUBLICATIONS

Zhen, "The Research on Ultrasonic Phased Array Imaging Technology", Feb. 15, 2013, 73 pages, B022-12.

Bao, "Research on Phased Array Ultrasonic Testing System and Its Key Technology", Jun. 15, 2004, 156 pages, C028-13.

Qin, "Study on Beamforming Algorithm of Ultrasound Imaging". Mar. 15, 2013, pp. 33-58, A005-31.

Thomenius, Kai E., Evolution of Ultrasound Beamformers; IEEE Ultrasonics Symposium, Nov. 3-6, 1996, pp. 1615-1622.

Freeman Steven R. et al., Delta-Sigma Oversampled Ultrasound Beanformer with Dynamic Delays, IEEE Transactions on Ultrasonics, Ferroelectrics, and Frequency Control, Mar. 1999, pp. 320-332, vol. 46, No. 2.

Kortbek Jacob et al., Comparing interpolation schemes in dynamic receive ultrasound beamforming, IEEE Ultrasonics Symposium, Sep. 18-21, 2005, pp. 1972-1975.

Sohn, H.-Y et al., Timesharing bilinear delay interpolation for ultrasound dynamic receive beamformer, Electronics Letters, Jan. 2011, pp. 89-91, vol. 47, No. 2.

Manes, G. et al., Synchronous Dynamic Focusing for Ultrasound Imaging, IEEE Transactions on Ultrasonics, Ferroelectrics, and Frequency Control, Jan. 1988, pp. 14-21, vol. 35, No. 1.

Li, Pai-Chi et al., Efficient Dynamic Focus Control for Three-Dimensional Imaging Using Two-Dimensional Arrays, IEEE Transactions on Ultrasonics, Ferroelectrics, and Frequency Control, Sep. 2002, pp. 1191-1202, vol. 49, No. 9.

McKeighen Ronald E. et al., New Techniques for Dynamically Variable Electronic Delays for Real Time Ultrasonic Imaging, Ultra Symposium Proceedings, 1977, pp. 250-254.

* cited by examiner

NONLINEAR DYNAMIC FOCUSING CONTROL METHOD

CROSS-REFERENCE TO RELATED APPLICATIONS

This application claims priority to Taiwanese Patent Application No. 102116164, filed on May 7, 2013. The entirety of the above-mentioned patent application is hereby incorporated by reference herein and made a part of this specification.

TECHNICAL FIELD

The present disclosure relates to a dynamic receiving focusing control method, and relates to a dynamic receiving focusing control method for nonlinearly distributed focal points.

BACKGROUND

Ultrasound images are widely used in the fields of biomedical and industrial inspection since they have the characteristics such as non-intrusiveness, real-time imaging and high image quality. Among ultrasound imaging systems, beamformers are the most critical. The so-called beamformer is located at the front end of the system for obtaining the electrical signals of the probe and performing delay control and associated signal processing. The quality of the signals after processing will have a significant impact on the application of the back end of the system, so that the designs of the beamformers are extremely important for imaging systems.

A traditional beamformer consists of two parts: a transmitting end and a receiving end. The transmitting end is used to control the transmission timing of each channel in an array transducer in order to achieve the effects of beam offset and focusing. The receiving end is used to provide receiving focus delay of various channels as well as to perform a delay sum. Since the focus delay of each channel is a function of the change in distance, in order to obtain a higher quality of the image, the value of the focus delay of each channel must be updated dynamically and each channel is given a different weight for adoptive adjustments to improve phase shifts as a result of ultrasound propagates at different speeds in different tissues.

Figure 1:
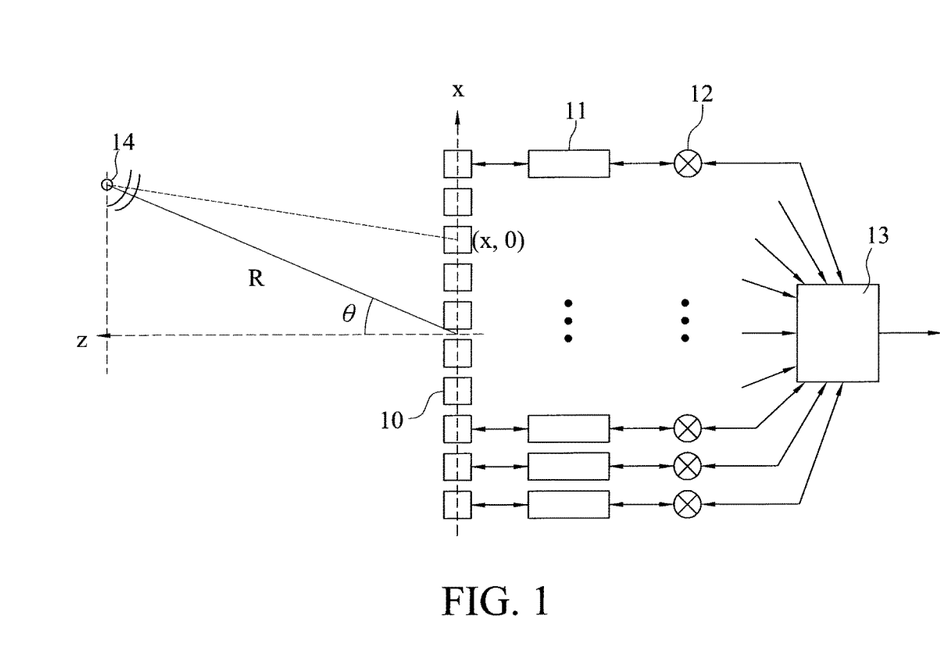
FIG. 1 is a schematic diagram illustrating a receiving end of an imaging system having an array transducer.

FIG. 1 is a schematic diagram illustrating a receiving end in an imaging system including an array transducer. The receiving end 1 includes an array transducer 10, delay units 11, weighting units 12, and a summing unit 13.

In order to calculate the focus delay of a focal point 14 to a channel at the location (x, 0), the following focus delay equation is used:

$$t_{rx} = \left(((R\sin\theta - x)^2 + (R\cos\theta)^2)^{1/2} - R\right)/c \approx -\frac{x\sin\theta}{c} + \frac{1}{R} \times \frac{x^2\cos^2\theta}{2c},$$

wherein $t_{rx}$ is the focus delay, R is the distance from the focal point 14 to the center point of the array transducer 10, θ is the angle between a line connecting the focal point 14 to the center point of the array transducer 10 and a z axis, and c is the speed of the wave.

However, dynamic focusing of the ultrasound imaging requires a large number of real-time computation and data transmission, and the calculation of which will be extremely complex. As an example, when the weight of each sampling point of a beamformer having 64 channels is calculated, a 64-by-64 matrix transpose operation will need to be carried out. Therefore, when the number of sampling points is increased in order to improve the image quality, its computational complexity will increase rapidly.

From the above, it is known that while the image quality of a traditional beamformer is improved, the number of channels of the array transducer or the number of sampling points of each channel is also increased, thus increasing the computational complexity of the system. Therefore, how to provide a beamformer design that is capable of reducing the computational complexity while maintaining a good image quality is a problem yet to be solved.

SUMMARY OF THE DISCLOSURE

The present disclosure is to provide a nonlinear dynamic focusing control method applicable to an imaging system with an array transducer, comprising: (1) selecting a scan line, wherein the scan line has a minimum length and a maximum length, and a focal point is assigned on the scan line using the minimum length as an initial location; (2) calculating a half depth of focus of the focal point, and the initial location plus the half depth of focus of the focal point being the location of this focal point on the scan line, wherein an equation for calculating the location of the focal point on the scan line is $$K \cdot \frac{\lambda}{A^2} z_{F,i}^2 - z_{F,i} + z_i = 0,$$

wherein $K \cdot \frac{\lambda}{A^2} z_{F,i}^2$ is the half depth of focus of the focal point, λ is the wavelength of the ultrasound transmitted by the imaging system, A is the aperture of the ultrasound transmitted by the imaging system, $z_{F,i}$ is the location of the focal point on the scan line, $z_i$ is the initial location, and K is a coefficient for adjusting the total number of focal points on the scan line; (3) determining an initial calculation location of the next focal point by adding the half depth of focus of the focal point from the location of this focal point on the scan line in the direction of the maximum length; and (4) determining if the initial calculation location of the next focal point is greater than the maximum length, if not, then replacing the initial location by the initial calculation location, and repeating steps (2) to (3); if so, then ending the calculation, wherein the locations of the focal points on the scan line are distributed nonlinearly based on the Shift Invariance (SI) characteristic of the Point Spread Function (PSF).

The present disclosure further provides a nonlinear dynamic focusing control method applicable to an imaging system with an array transducer, comprising: (1) selecting a scan line, wherein the scan line has a minimum length and a maximum length; (2) defining at least one knee point on the scan line to segment the scan line into n scan segments, wherein n is not less than 2, and the n scan segments are arranged sequentially along the scan line from the minimum length to the maximum length, a first scan segment in the n scan segments has an initial location at the minimum length and an ending location at the knee point closest to the minimum length, a second scan segment in the n scan segments has an ending location at the maximum length and an initial location at the knee point closest to the maximum length, and the rest of scan segments begin at knee points closest to the minimum length and have two adjacent knee points as the initial locations and the ending locations, and a focal point is assigned on each of the scan segments; (3) calculating half depth of focus of the focal point of each scan segment, and the initial location of each scan segment plus the half depth of focus of the focal point of the corresponding scan segment being the location of the focal point of this scan segment on the scan line, wherein an equation for calculating the location of the focal point on each scan segment is $$K \cdot \frac{\lambda}{A^2} z_{F,i}^2 - z_{F,i} + z_i + \Delta z_i = 0,$$

wherein $K \cdot \frac{\lambda}{A^2} z_{F,i}^2$ is the half depth of focus of the focal point, $\lambda$ is the wavelength of the ultrasound transmitted by the imaging system, A is the aperture of the ultrasound transmitted by the imaging system, $z_{F,i}$ is the location of the focal point on the scan line, $z_i$ is the initial location, $\Delta z_i$ is a correction term for adjusting the location of the focal point on the scan line, and K is a coefficient for adjusting the total number of focal points on the scan line; (4) determining initial calculation locations of the next focal points of the respective scan segments by adding the half depth of focus of the respective focal points to the locations of the respective focal points on the respective scan segments in the direction of the maximum length, respectively; and (5) determining if the initial calculation locations of the next focal points on the respective scan segments are greater than the maximum length, respectively, if not, then replacing the initial location of the scan segment by the initial calculation location of the scan segment, and repeating steps (3) to (4); if so, then ending the calculation of this scan segment, wherein the locations of the focal points on the scan line are distributed nonlinearly based on the Shift Invariance (SI) characteristic of the Point Spread Function (PSF), and $\Delta z_i$ of at least one of the scan segments is different from the others.

Compared to the prior art, the nonlinear dynamic focusing control method of the present disclosure allows the focal points to be distributed nonlinearly based on the SI characteristic of the PSF, so that focal points can be arranged more efficiently. The depth of focus ranges extending from the focal points as the centers form weighted blocks, and sampling points within the same weighted block are given the same weights, thereby reducing the computational complexity.

BRIEF DESCRIPTION OF THE DRAWINGS

The present disclosure can be more fully understood by reading the following detailed description of the preferred embodiments, with reference made to the accompanying drawings, wherein.

DETAILED DESCRIPTION OF THE EMBODIMENTS

The present disclosure is described by the following specific embodiments. Those with ordinary skills in the arts can readily understand the other advantages and functions of the present disclosure after reading the present disclosure of this specification. The present disclosure can also be implemented or applied in other different embodiments. The various details of the present application may also be modified or changed based on different viewpoints and applications without departing from the spirit of the present disclosure.

Figure 2A:
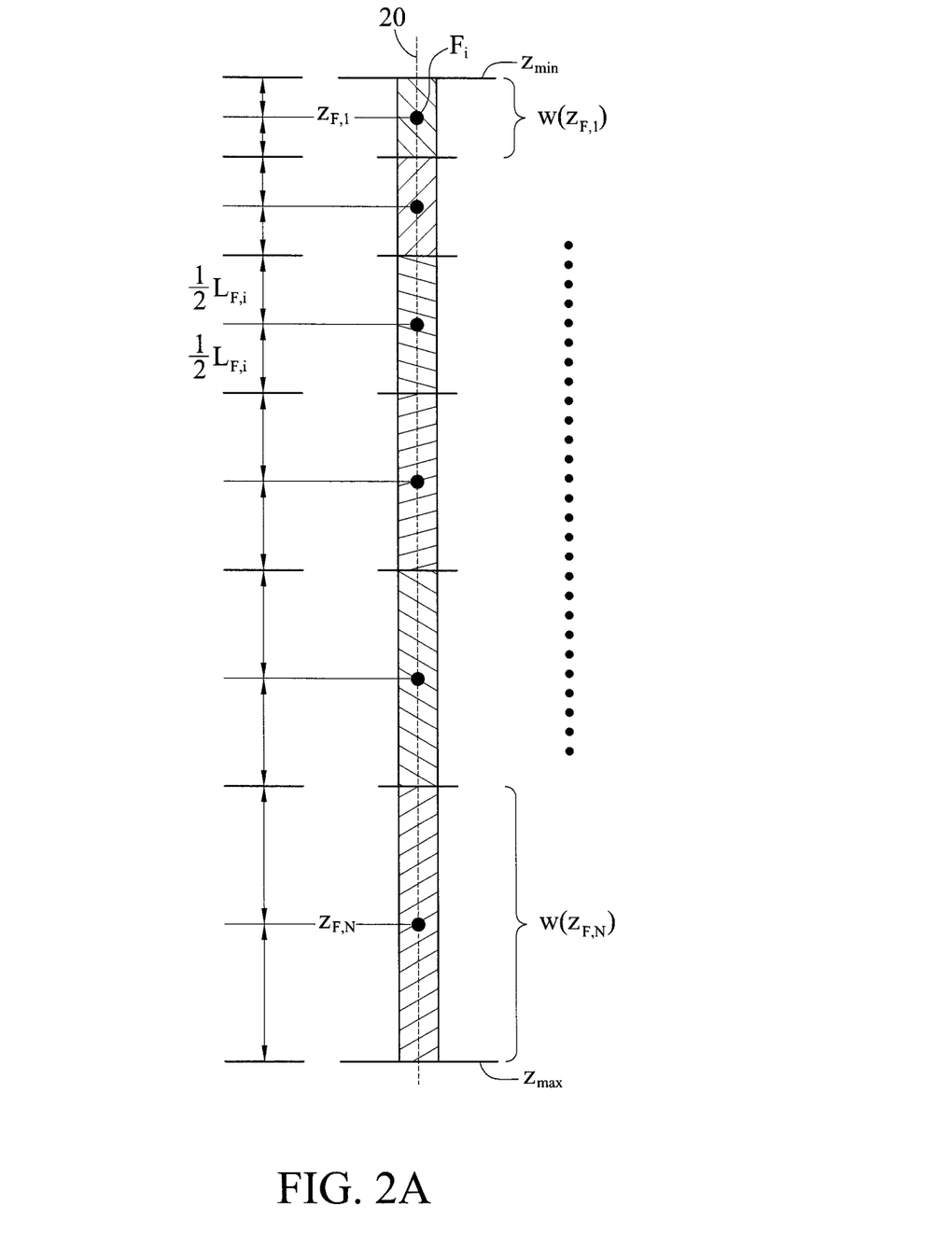
FIG. 2A is a schematic diagram illustrating an embodiment of a nonlinear dynamic focusing control method in accordance with the present disclosure after completing the calculation and arrangement of focal points.

FIG. 2A is a schematic diagram illustrating a nonlinear dynamic focusing control method in accordance with an embodiment of the present disclosure after completing the calculation and arrangement of focal points. As shown in the diagram, these focal points $F_i$ (i is from 1 to N) are distributed at locations $z_{F,1}$ to $z_{F,N}$ on a scan line 20 having a minimum length $z_{min}$ and a maximum length $z_{max}$, wherein weighted blocks $w(z_{F,1})$ to $w(z_{F,N})$ are formed by extending from each of the focal points at the locations $z_{F,1}$ to $z_{F,N}$ on the scan line 20 as the center half depth of focus $\frac{1}{2}L_{F,i}$ corresponding to each focal point $F_i$ in directions towards the minimum length $z_{min}$ and the maximum length $z_{max}$.

Figure 2B:
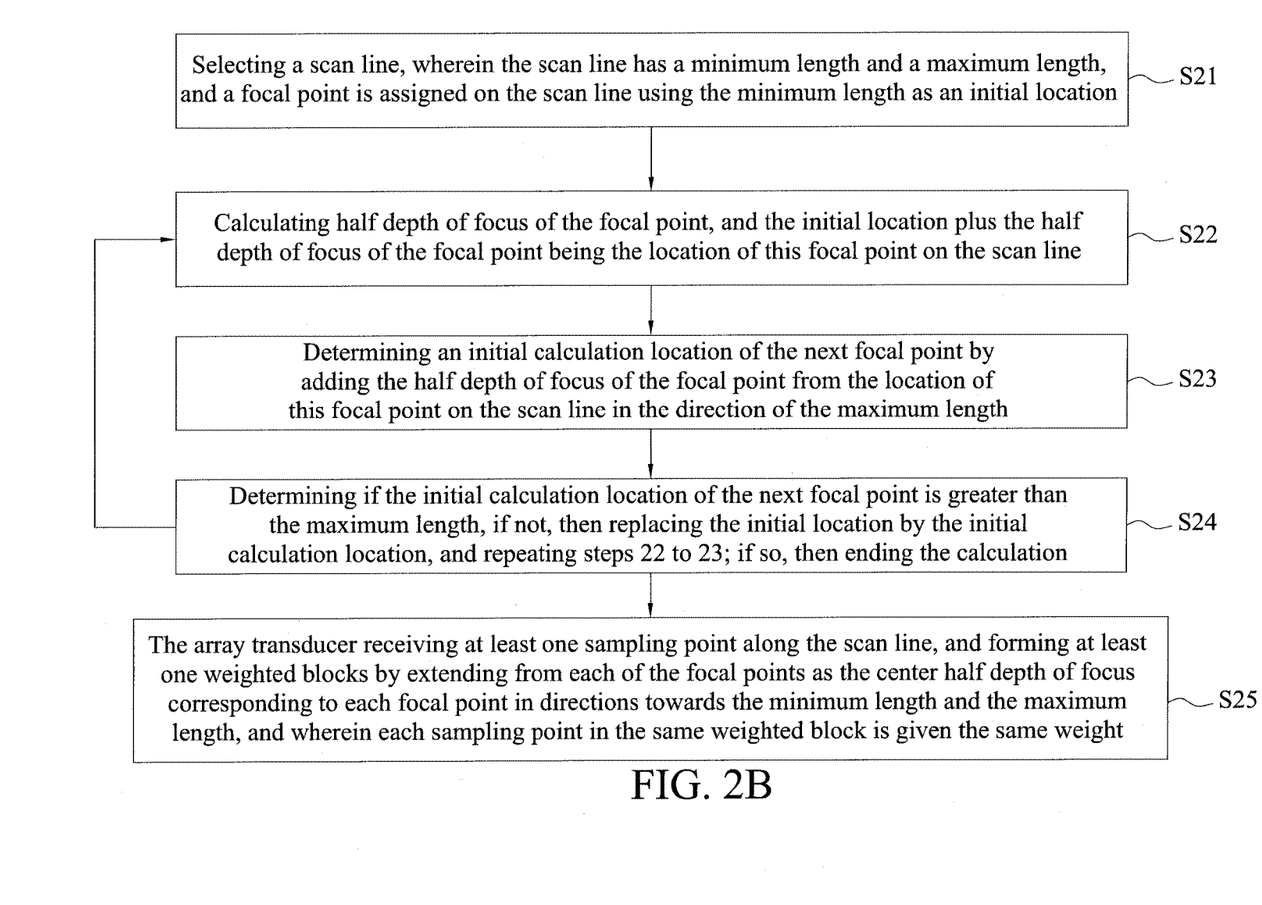
FIG. 2B is a flowchart illustrating an embodiment of the nonlinear dynamic focusing control method in accordance with the present disclosure.

FIG. 2B is a flowchart illustrating the nonlinear dynamic focusing control method in accordance with an embodiment of the present disclosure. As shown, the method includes the following steps.

In step S21, a scan line 20 is selected, wherein the scan line 20 has a minimum length $z_{min}$ and a maximum length $z_{max}$, and a focal point $F_i$ is assigned on the scan line 20 using the minimum length $z_{min}$ as an initial location $z_i$.

In step S22, the half depth of focus $\frac{1}{2}L_{F,i}$ of the focal point $F_i$ is calculated, and the initial location $z_i$ plus the half depth of focus of the focal point $F_i$ is the location of this focal point $z_{F,i}$ on the scan line 20, wherein the equation for calculating the location of the focal point on the scan line is $$K \cdot \frac{\lambda}{A^2} z_{F,i}^2 - z_{F,i} + z_i = 0,$$

-continued $$K \cdot \frac{\lambda}{A^2} z_{F,i}^2 = \frac{1}{2} L_{F,i}$$

is the half depth of focus of the focal point, $\lambda$ is the wavelength of the ultrasound transmitted by the imaging system, A is the aperture of the ultrasound transmitted by the imaging system, $z_{F,i}$ is the location of the focal point on the scan line, $z_i$ is the initial location, and K is a coefficient for adjusting the total number of focal points on the scan line.

In one embodiment, $$z_{F,i} = \frac{-(-1) \pm \sqrt{(-1)^2 - 4\left(K \cdot \frac{\lambda}{A^2}\right) z_i}}{2\left(K \cdot \frac{\lambda}{A^2}\right)}$$

can be obtained by solving the equation for calculating the location of the focal point on the scan line $$K \cdot \frac{\lambda}{A^2} z_{F,i}^2 - z_{F,i} + z_i = 0,$$

wherein only one solution will be between the initial location and the maximum length, and thus step S22 further includes confirming that the location of the focal point $F_i$ on the scan line 20 is greater than the initial location $z_i$ and less than the maximum length $z_{max}$.

In another embodiment, step S22 further includes comparing the half depth of focus $½L_{F,i}$ of the focal point $F_i$ with a preset sample duration of the imaging system. If the half depth of focus $½ L_{F,i}$ of the focal point $F_i$ is smaller than the preset sample duration, then the half depth of focus of the focal point is replaced by the sample duration.

In step S23, an initial calculation location $z_i'$ of the next focal point is determined by adding the half depth of focus $½ L_{F,i}$ of the focal point $F_i$ from the location $z_{F,i}$ of this focal point on the scan line in the direction of the maximum length $z_{max}$.

In step S24, it is determined whether the initial calculation location $z_i'$ of the next focal point is greater than the maximum length $z_{max}$. If not, then the initial location $z_i'$ is replaced by the initial calculation location $z_i'$, and steps S22 to S23 are repeated; if so, then the calculation is ended and step S25 is performed.

Figure 2C:
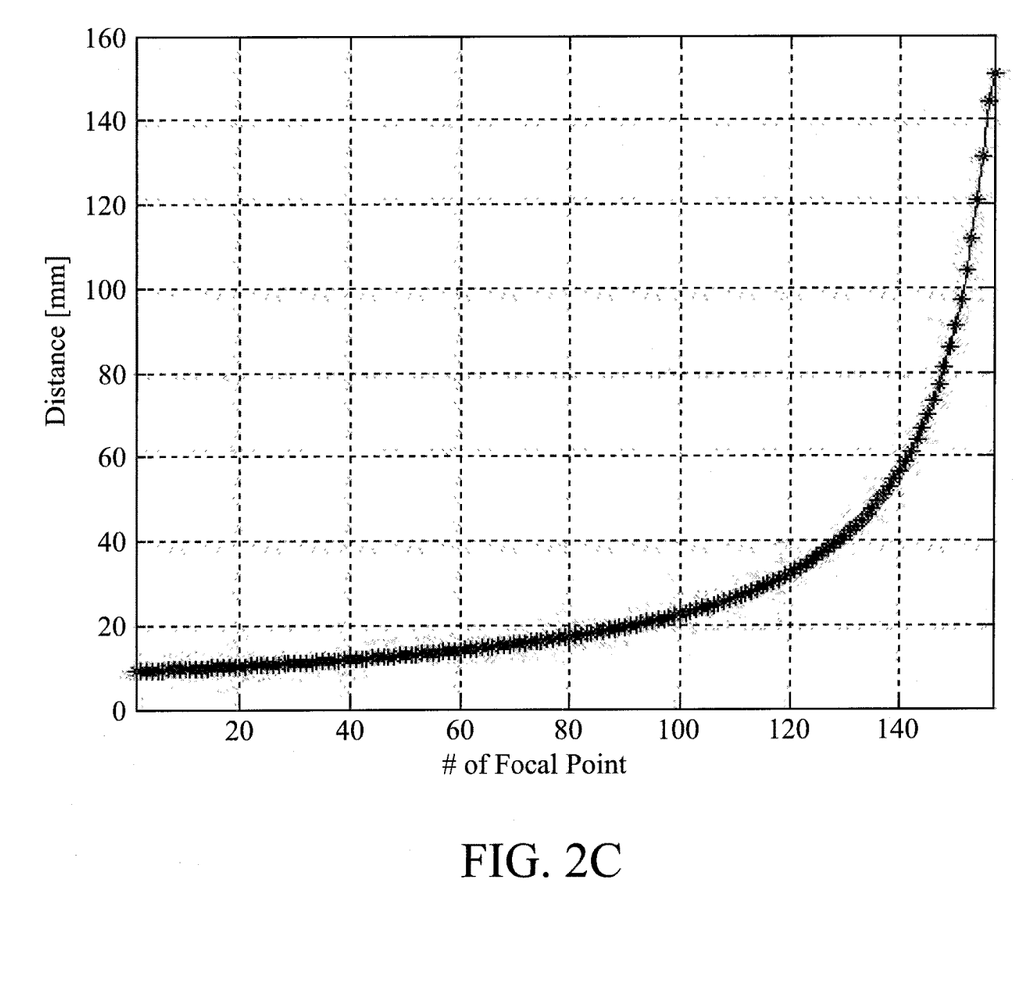
FIG. 2C is a chart illustrating a distribution of the locations of focal points in an embodiment of the nonlinear dynamic focusing control method in accordance with the present disclosure.

In this embodiment, the locations of the focal points on the scan line are distributed in a non linear fashion according to the Shift Invariance (SI) characteristic of the Point Spread Function (PSF). For example, this nonlinear distribution is a second-order nonlinear distribution, as can be seen from FIG. 2C.

Figure 2D:
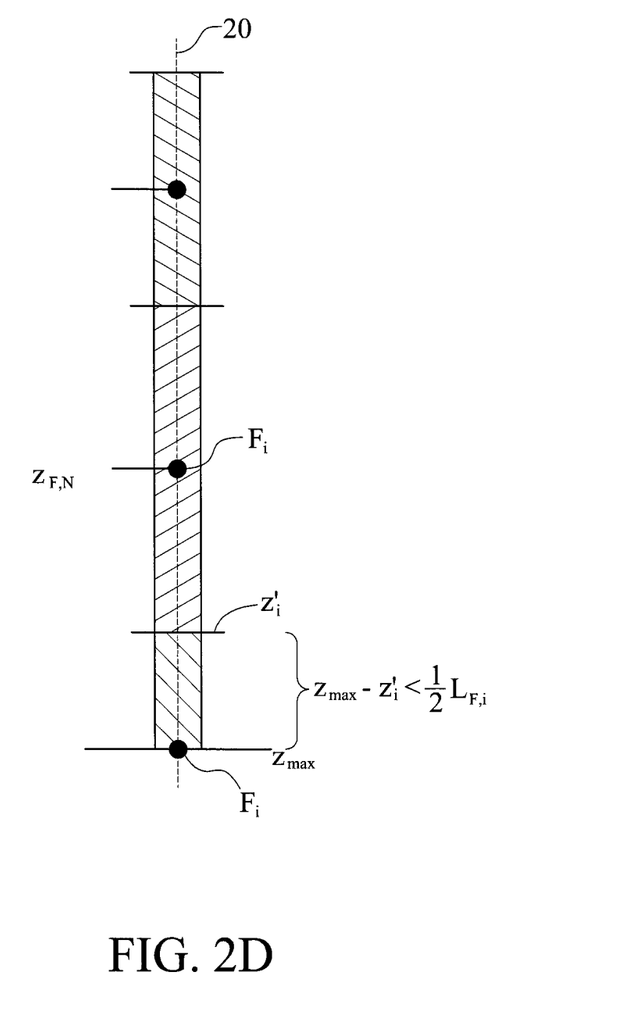
FIG. 2D is a schematic diagram illustrating a focal point located on a maximum length in an embodiment of the nonlinear dynamic focusing control method in accordance with the present disclosure.

In an embodiment, step S24 further includes when the initial calculation location $z_i'$ of the next focal point is smaller than the maximum length $z_{max}$ and the maximum length $z_{max}$ minus the initial calculation location $z_i'$ of the next focal point is smaller than the half depth of focus $½ L_{F,i}$ of the next focal point, assigning the next focal point on the maximum length $z_{max}$, as shown in FIG. 2D.

Figure 2E:
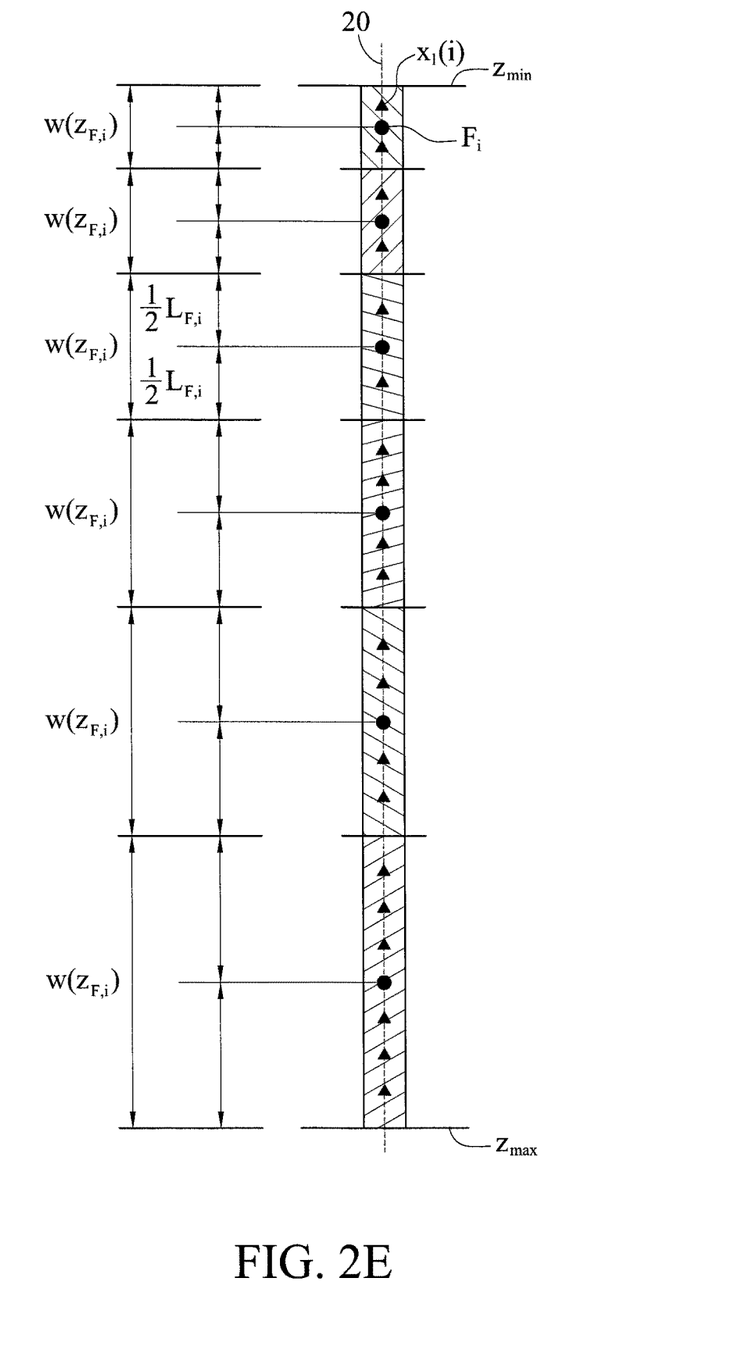
FIG. 2E is a schematic diagram illustrating weighted blocks in the nonlinear dynamic focusing control method in accordance with an embodiment of the present disclosure.

In step S25, an array transducer receives at least one sampling point $x_i(i)$ along the scan line 20, and forms at least one weighted blocks $w(z_{F,i})$ by extending from each of the focal points $F_i$ at the locations $z_{F,i}$ on the scan line as the center half depth of focal $½L_{F,i}$ corresponding to each focal point $z_{F,i}$ in directions towards the minimum length $z_{min}$ and the maximum length $z_{max}$, and each sampling point $x_i(i)$ in the same weighted block $w(z_{F,i})$ is given the same weight, thereby reducing the computational complexity, as shown in FIG. 2E.

Figure 3A:
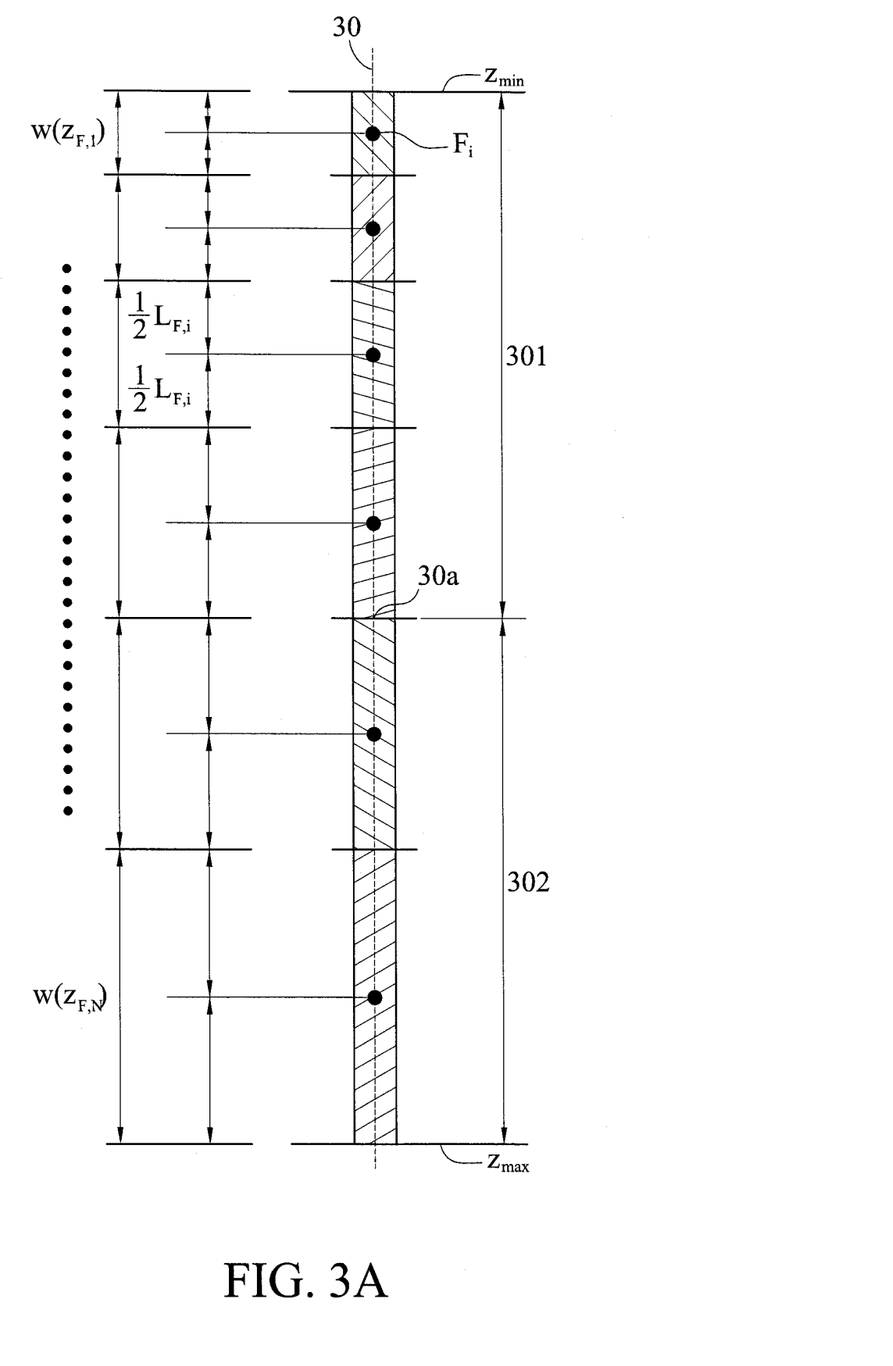
FIG. 3A is a schematic diagram illustrating a nonlinear dynamic focusing control method in accordance with another embodiment of the present disclosure after completing the calculation and arrangement of focal points.

FIG. 3A is a schematic diagram illustrating the nonlinear dynamic focusing control method in accordance with another embodiment of the present disclosure after completing the calculation and arrangement of focal points. As shown in the diagram, focal points $F_i$ (i is from 1 to N) are distributed at locations $z_{F,1}$ to $z_{F,N}$ on a scan line 30 having a minimum length $z_{min}$ and a maximum length $z_{max}$, and a knee point 30a on the scan line 30 breaks the scan line 30 into two segments: a first scan segment 301 and a second scan segment 302, wherein weighted blocks $w(z_{F,1})$ to $w(z_{F,N})$ are formed by extending from each of the focal points $F_i$ at the locations $z_{F,1}$ to $z_{F,N}$ on the scan line 30 as the center half depth of focus $½L_{F,i}$ corresponding to each focal point $F_i$ in directions towards the minimum length $z_{min}$ and the maximum length $z_{max}$.

Figure 3B:
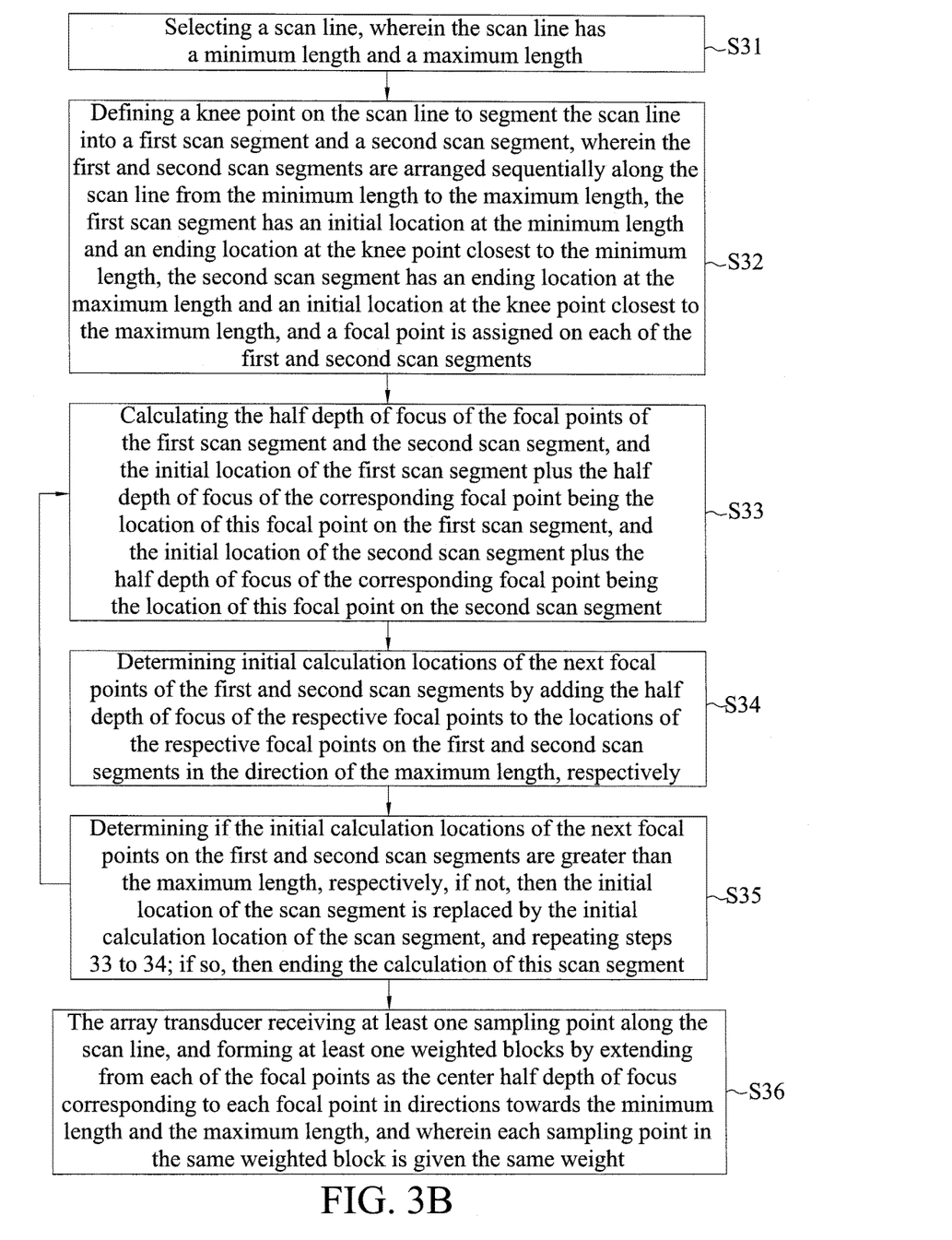
FIG. 3B is a flowchart illustrating the nonlinear dynamic focusing control method in accordance with another embodiment of the present disclosure.

FIG. 3B is a flowchart illustrating the nonlinear dynamic focusing control method in accordance with another embodiment of the present disclosure. As shown, the method includes the following steps.

In step S31, a scan line 30 is selected, wherein the scan line 30 has a minimum length $z_{min}$ and a maximum length $z_{max}$.

In step S32, a knee point 30a is defined on the scan line 30 to segment the scan line 30 into a first scan segment 301 and a second scan segment 302, wherein the first scan segment 301 and the second scan segment 302 are arranged sequentially along the scan line 30 from the minimum length $z_{min}$ to the maximum length $z_{max}$, the first scan segment 301 has an initial location $z_i$ at the minimum length $z_{min}$ and an ending location $z_{End}$ at the knee point 30a closest to the minimum length $z_{min}$, whereas the second scan segment 302 has an ending location $z_{End}$ at the maximum length $z_{max}$ and an initial location $z_i$ at the knee point 30a closest to the maximum length $z_{max}$, and focal points $F_i$ are assigned on the first scan segment 301 and the second scan segment 302. In this embodiment, only one knee point is shown as an example, but the present disclosure is not limited as such, rather there can be a plurality of knee points segmenting the scan line into a plurality of segments.

In one implementation, the knee point 30a is a junction point of a near range and a far range or a transmit focus, however, the knee point of the present disclosure is not limited as such and can be determined arbitrary according to different applications.

In step S33, half depth of focus $½L_{F,i}$ of the focal points $F_i$ of the first scan segment 301 and the second scan segment 302 are calculated, and the initial location $z_i$ of the first scan segment 301 plus the half depth of focus $½L_{F,i}$ of the corresponding focal point $F_i$ is the location of this focal point $z_{F,i}$ on the first scan segment 301, and the initial location $z_i$ of the second scan segment 302 plus the half depth of focus $½L_{F,i}$ of the corresponding focal point $F_i$ is the location of this focal point $z_{F,i}$ on the second scan segment 302, wherein the equation for calculating the location of the focal point on each scan segment is $$K \cdot \frac{\lambda}{A^2} z_{F,i}^2 - z_{F,i} + z_i + \Delta z_i = 0,$$

-continued $$\text{wherein } K \cdot \frac{\lambda}{A^2} z_{F,i}^2 = \frac{1}{2} L_{F,i}$$

is the half depth of focus of each focal point, $\lambda$ is the wavelength of the ultrasound transmitted by the imaging system, A is the aperture of the ultrasound transmitted by the imaging system, $z_{F,i}$ is the location of the focal point on the scan line, $z_i$ is the initial location, $\Delta z_i$ is a correction term for adjusting the location of the focal point on the scan line, and K is a coefficient for adjusting the total number of focal points on the scan line.

Figure 3C:
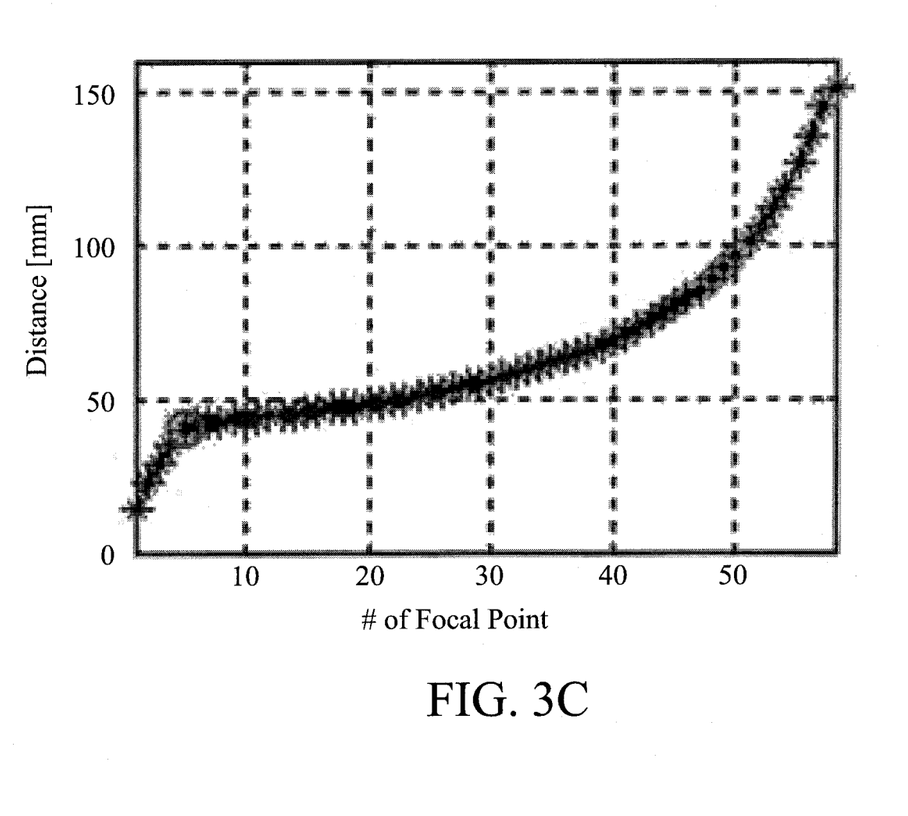
FIG. 3C is a chart illustrating a distribution of the locations of focal points in the nonlinear dynamic focusing control method in accordance with another embodiment of the present disclosure.

In one implementation, the focal points on the scan segments can be distributed in a linear, second-order nonlinear, third-order nonlinear or higher-order nonlinear fashion by adjusting $\Delta z_i$ in the equation for calculating the location of the focal point on each scan segment $$K \cdot \frac{\lambda}{A^2} z_{F,i}^2 - z_{F,i} + z_i + \Delta z_i = 0,$$

so the distribution of the focal points on the entire scan line can be a compounded nonlinear distribution as shown in FIG. 3C.

In another embodiment, step S33 further includes comparing the half depth of focus $\frac{1}{2}L_{F,i}$ of the focal point $F_i$ with a preset sample duration of the imaging system. If the half depth of focus $\frac{1}{2}L_{F,i}$ of the focal point $F_i$ is smaller than the preset sample duration, then the half depth of focus of the focal point is replaced by the sample duration.

In step S34, initial calculation locations $z_i'$ of the next focal points are determined by adding the half depth of focus $\frac{1}{2}L_{F,i}$ of the focal points $F_i$ to the respective locations $z_{F,i}$ of the focal points $F_i$ on the first and second scan segments 301 and 302 in the direction of the maximum length $z_{max}$, respectively.

In step S35, it is determined whether the initial calculation locations $z_i'$ of the next focal points on the first and the second scan segments 301 and 302 are greater than the maximum length $z_{max}$, respectively. If not, then the initial location $z_i$ of the scan segment is replaced by the initial calculation location $z_i'$ of the scan segment, and steps S33 to S34 are repeated; if so, then the calculation of the scan segment is ended and step S36 is performed.

In this embodiment, the locations of the focal points on the scan line 30 are distributed in a non linear fashion according to the Shift Invariance (SI) characteristic of the Point Spread Function (PSF), and $\Delta z_i$ in the first scan segment is different from that in the second scan segment, that is, the nonlinear distribution is a compounded nonlinear distribution as shown in FIG. 3C [C1].

In step S36, an array transducer receives at least one sampling point $x_i(i)$ along the scan line, and forms at least one weighted blocks $w(z_{F,i})$ by extending from each of the focal points $F_i$ at the locations $z_{F,i}$ on the scan line as the center half depth of focus $\frac{1}{2}L_{F,i}$ corresponding to each focal point $z_{F,i}$ in directions towards the minimum length $z_{min}$ and the maximum length $z_{max}$, and each sampling point $x_i(i)$ in the same weighted block $w(z_{F,i})$ is given the same weight, thereby reducing the computational complexity.

In summary, the nonlinear dynamic focusing control method of the present disclosure allows the focal points to be distributed nonlinearly based on the SI characteristic of the PSF, so focal points can be arranged more efficiently. The depth of focus ranges extending from the focal points as the centers form weighted blocks, and sampling points within the same weighted block are given the same weights, thereby reducing the computational complexity, and satisfying the needs for low system complexity and high image quality for ultrasound focusing imaging.

The above embodiments are only used to illustrate the principles of the present disclosure, and should not be construed as to limit the present disclosure in any way. The above embodiments can be modified by those with ordinary skill in the art without departing from the scope of the present disclosure as defined in the following appended claims.

What is claimed is:

1. A nonlinear dynamic focusing control method applicable to an imaging system with an array transducer, comprising:
   (1) adding, by an adder, a minimum length of a scan line as an initial location of the scan line with a half depth of focus of a focal point on the scan line as the location of the focal point on the scan line;
   (2) adding, by the adder, the half depth of focus of the focal point with the location of the focal point on the scan line in a direction of a maximum length of the scan line to form an initial calculation location of a next focal point;
   (3) comparing, by a comparator, the initial calculation location of the next focal point with the maximum length; and
   (4) replacing the initial location by the initial calculation location and repeating steps (2) to (3) when the initial calculation location of the next focal point is less than the maximum length,
   wherein the locations of the focal points on the scan line are nonlinear distribution.

2. The nonlinear dynamic focusing control method of claim 1, wherein an equation for calculating the location of the focal point on the scan line is $$K \cdot \frac{\lambda}{A^2} z_{F,i}^2 - z_{F,i} + z_i = 0,$$

$$\text{wherein } K \cdot \frac{\lambda}{A^2} z_{F,i}^2$$

is the half depth of focus of the focal point, $\lambda$ is the wavelength of the ultrasound transmitted by the imaging system, A is the aperture of the ultrasound transmitted by the imaging system, $z_{F,i}$ is the location of the focal point on the scan line, $z_i$ is the initial location, and K is a coefficient for adjusting the total number of focal points on the scan line.

3. The nonlinear dynamic focusing control method of claim 1, wherein the nonlinear distribution is a second-order nonlinear distribution.

4. The nonlinear dynamic focusing control method of claim 1, wherein the location of the focal point on the scan line is greater than the initial location and less than the maximum length.

5. The nonlinear dynamic focusing control method of claim 1, wherein step (1) further includes comparing, by the comparator, the half depth of focus of the focal point with a preset sample duration of the imaging system, sample duration, then replacing the half depth of focus of the focal point is replaced by the sample duration when the half depth of focus of the focal point is smaller than the preset sample duration.

6. The nonlinear dynamic focusing control method of claim 1, wherein the initial calculation location of the next focal point is smaller than the maximum length, the maximum length minus the initial calculation location of the next focal point is smaller than the half depth of focus of the next focal point, and step (3) further comprises setting the next focal point to be the maximum length.

7. The nonlinear dynamic focusing control method of claim 1, further comprising:
(5) receiving by the array transducer at least one sampling point along the scan line, and weighing the sampling point with a weight according to a weight block within which the sampling point is located, wherein the weighted block is formed by extending from each of the focal points at the locations on the scan line as the center half depth of focus corresponding to each focal point in directions towards the minimum length and the maximum length, wherein each sampling point in and sampling points within the same weighted block are given the same weight for beamforming.

8. A nonlinear dynamic focusing control method applicable to an imaging system with an array transducer, comprising:
(1) defining at least one knee point on a scan line that has a maximum length and a minimum length to segment the scan line into n scan segments, wherein n is not less than 2, and the n scan segments are arranged sequentially along the scan line from the minimum length to the maximum length, a first scan segment in the n scan segments has an initial location at the minimum length and an ending location at the knee point closest to the minimum length, a second scan segment in the n scan segments has an ending location at the maximum length and an initial location at the knee point closest to the maximum length, the rest of scan segments begin at knee points closest to the minimum length and have two adjacent knee points as the initial locations and the ending locations, and a focal point is assigned on each of the scan segments;
(2) adding, by an adder, the initial location of each scan segment with the half depth of focus of the focal point of the corresponding scan segment as the location of the focal point of this scan segment on the scan line;
(3) adding, by the adder, the half depth of focus of the respective focal points with the locations of the respective focal points on the respective scan segments in the direction of the maximum length, respectively, to form initial calculation locations of the next focal points of the respective scan segments;
(4) comparing, by a comparator, the initial calculation locations of the next focal points on the respective scan segments with the maximum length; and
(5) replacing the initial location of the scan segment by the initial calculation location of the scan segment and repeating steps (3) to (4) when the initial calculation locations of the next focal points on the respective scan segments are less than the maximum length,
wherein the locations of the focal points on the scan line are nonlinear distribution, and $\Delta z_i$ of at least one of the scan segments is different from the others.

9. The nonlinear dynamic focusing control method of claim 8, wherein an equation for calculating the location of the focal point on each scan segment is $$K \cdot \frac{\lambda}{A^2} z_{F,i}^2 - z_{F,i} + z_i + \Delta z_i = 0,$$

wherein $K \cdot \frac{\lambda}{A^2} z_{F,i}^2$ is the half depth of focus of the focal point, $\lambda$ is the wavelength of the ultrasound transmitted by the imaging system, A is the aperture of the ultrasound transmitted by the imaging system, $z_{F,i}$ is the location of the focal point on the scan line, $z_i$ is the initial location, $\Delta z_i$ is a correction term for adjusting the location of the focal point on the scan line, and K is a coefficient for adjusting the total number of focal points on the scan line.

10. The nonlinear dynamic focusing control method of claim 8, wherein the focal points on the scan segments are distributed in a linear, second-order nonlinear, third-order nonlinear or higher-order nonlinear fashion by adjusting $\Delta z_i$ in the equation for calculating the location of the focal point on each scan segment.

11. The nonlinear dynamic focusing control method of claim 8, wherein the location of the focal point on the respective scan segment is greater than the initial location and less than the ending location.

12. The nonlinear dynamic focusing control method of claim 8, wherein step (2) further includes comparing, by the comparator, the half depth of focus of the focal point with a preset sample duration of the imaging system, and replacing the half depth of focus of the focal point by the sample duration when the half depth of focus of the focal point is smaller than the preset sample duration.

13. The nonlinear dynamic focusing control method of claim 8, wherein the initial calculation location of the next focal point of the $n^{th}$ scan segment is smaller than the maximum length, the maximum length minus the initial calculation location of the next focal point of the $n^{th}$ scan segment is smaller than the half depth of focus of the next focal point of the $n^{th}$ scan segment, and step (4) further comprises setting the next focal point of the $n^{th}$ scan segment on the maximum length.

14. The nonlinear dynamic focusing control method of claim 8, further comprising:
(6) receiving by the array transducer at least one sampling point along the scan line, and weighing the sampling point with a weight according to a weighted block within which the sampling point is located, wherein the weighted block is formed by extending from each of the focal points as the center half depth of focus corresponding to each focal point in directions towards the minimum length and the maximum length, and sampling points within the same weighted block are given the same weight for beamforming.

15. The nonlinear dynamic focusing control method of claim 8, wherein the knee point is a junction point of a near range and a far range or a transmit focus.

* * * * *